United States Patent [19]
Lubell et al.

[11] Patent Number: 6,159,016
[45] Date of Patent: *Dec. 12, 2000

[54] METHOD AND SYSTEM FOR PRODUCING PERSONAL GOLF LESSON VIDEO

[76] Inventors: Alan Lubell, 15 W. 81$^{st}$ St., New York, N.Y. 10024; Thomas S. Peters, 630 SW. 18$^{th}$ St., Boca Raton, Fla. 33486; Earl Takefman, 68 Belvedere, Montreal, Quebec, Canada, H36 1P8

[ * ] Notice: This patent is subject to a terminal disclaimer.

[21] Appl. No.: 08/994,972

[22] Filed: Dec. 19, 1997

Related U.S. Application Data

[60] Provisional application No. 60/033,869, Dec. 20, 1996, and provisional application No. 60/037,388, Feb. 7, 1997.

[51] Int. Cl.$^7$ .............................. A63B 69/00; A63B 69/36
[52] U.S. Cl. ............................................ 434/247; 434/252
[58] Field of Search ..................................... 434/247–258; 345/328; 473/131, 266, 409

[56] References Cited

U.S. PATENT DOCUMENTS

| | | | |
|---|---|---|---|
| 3,145,484 | 8/1964 | Bayley ..................... | 434/257 |
| 3,408,750 | 11/1968 | McCollough et al. .................. | 473/266 |
| 4,005,261 | 1/1977 | Sato et al. ............... | 434/252 |
| 4,009,331 | 2/1977 | Goldmark et al. ........................ | 368/38 |
| 4,015,344 | 4/1977 | Michaels et al. ........................ | 434/257 |
| 4,137,566 | 1/1979 | Haas et al. .............................. | 473/209 |
| 4,163,941 | 8/1979 | Linn, Jr. ................................... | 324/178 |
| 4,713,686 | 12/1987 | Ozaki et al. ............................ | 348/157 |
| 4,797,805 | 1/1989 | Lubell et al. ........................... | 473/266 |
| 4,828,500 | 5/1989 | Seidel et al. ............................ | 434/247 |
| 4,839,733 | 6/1989 | Karamon et al. ......................... | 360/13 |
| 4,891,748 | 1/1990 | Mann ...................................... | 473/266 |
| 5,046,097 | 9/1991 | Lowe et al. ............................... | 381/17 |
| 5,111,410 | 5/1992 | Nakayama et al. ..................... | 473/221 |
| 5,184,295 | 2/1993 | Mann ..................................... | 473/221 |
| 5,210,603 | 5/1993 | Sabin ..................................... | 348/157 |
| 5,249,967 | 10/1993 | O'Leary et al. ........................ | 473/267 |
| 5,297,796 | 3/1994 | Peterson ................................ | 473/266 |
| 5,333,061 | 7/1994 | Nakashima et al. .................... | 358/335 |
| 5,342,054 | 8/1994 | Chang et al. ........................... | 473/156 |
| 5,486,001 | 1/1996 | Baker ..................................... | 473/266 |
| 5,506,639 | 4/1996 | Frazen et al. ............................ | 352/12 |
| 5,823,786 | 10/1998 | Easterbrook ........................... | 434/247 |
| 5,857,855 | 1/1999 | Katayama .............................. | 434/247 |

*Primary Examiner*—Kien Nguyen
*Assistant Examiner*—John Edmund Rovnak
*Attorney, Agent, or Firm*—Baker & McKenzie

[57] ABSTRACT

A system and method for producing a personal golf lesson videotape from a visual recording of a person's golf swing and a partially prerecorded instructional golf lesson videotape. The partially prerecorded golf lesson videotape has gaps in predetermined locations into which are inserted the full motion video of the person's golf swing and selected still frames. The system contains two cameras for recording a player's golf swing from the back and side, a computer connected to the cameras for digitally capturing and storing the recorded golf swing, and a computer-controlled video recording device for copying the selected video and still frames of the recorded golf swing into the gaps of the prerecorded videotape golf lesson. The still frames are selected to match the player's position to the position of the professional golfer in corresponding still frames so that a split screen, side-by-side view can be produced showing the player's and professional's positions at various points along a golf swing.

24 Claims, 12 Drawing Sheets

METHOD AND SYSTEM FOR PRODUCING PERSONAL GOLF LESSON VIDEO

This application claims the benefit of U.S. Provisional Application Nos. 60/033,869, and 60/037,388 filed Dec. 20, 1996, and Feb. 7, 1997, respectively.

REFERENCE TO RELATED APPLICATION

This application incorporates by reference, as if fully restated here, application Ser. No. 08/656,156, filed May 24, 1996, by Lubel et al., for "Method and System for Producing Personal Golf Lesson Video" and now U.S. Pat. No. 5,797,805, granted Aug. 25, 1998.

COPYRIGHT NOTICE

A portion of the disclosure of this patent document contains material that is subject to copyright protection. The copyright owner has no objection to the facsimile reproduction by anyone of the patent disclosure, as it appears in the United States Patent and Trademark Office patent files or records, but otherwise reserves all copyright rights whatsoever.

BACKGROUND OF THE INVENTION

This invention relates generally to an instructional system for teaching how best to execute a sport by visually recording a person's performance in the sport and comparing the execution to a model. In particular, this invention relates to a system and method that quickly and economically creates high quality, complete personalized, individualized and customized videotape lessons for large groups with little human intervention.

Form, body position, and execution are important ingredients to success in all sports. The best way to achieve success is under the direction of a professional instructor who can observe the athlete's execution and correct the athlete's position and motion. The athlete's execution can even be video recorded and reviewed later by the athlete and/or the instructor.

In the sport of golf, systems have been proposed to record a golfer's swing and then analyze the swing according to precise principles. For example, a system described in U.S. Pat. No. 5,333,061 to Nakashima et al. converts recorded video images of a golfer's swing into a plurality of still images and superimposes on the still images correction pictures consisting of a series of lines connecting various points on the golfer's body and club. The resulting pictures are then recorded onto a videotape, and additional visual and/or audio information can then be added to the videotape.

Similarly, U.S. Pat. No. 5,111,410 to Nakayama et al. describes a motion diagnosis system in which retro-reflective tape is pasted onto a plurality of points on a golfer's body and golf club, the golfer's golf swing is recorded, images of the swing are sampled and converted to digital signals, and positional data is extracted from the plurality of points to which the tape was pasted. The positional data is then compared to reference data to create a diagnosis of the golfer's swing based on the difference between the positional and reference data.

As yet a further example, a system described in U.S. Pat. No. 4,891,748 to Mann captures a video image of a golf student's swing, generates a superior performance model golf player having physical dimensions scaled to those of the golfer, and overlays the image of the model onto the image of the student. The model is computer generated and includes composite average swing movements of a plurality of golf players, enhanced using statistical identification of the critical performance patterns of the swing.

U.S. Pat. No. 5,486,001 to Baker is still another example of a system for producing a personalized golf video. Baker discloses an instructional system in which previously recorded instructional material of a non-personalized nature may be added to a video cassette, and regenerated signals of a pupil's audio-visual presentation may be then simply added to the prerecorded material. The resulting single recording then shows (a) an initial complete recorded procedure of instruction, as currently presented with audio-visual presentations; (b) an addition of their current movements, procedures, images etc. taken before regeneration; and (c) the final regenerated personalized audio-visual changes.

Successful instructors recognize that instruction must be tailored to the student. For example, well known to golf instructors is that although each golfer's swing may be unique, golf instruction must be customized to the golfer and different instructional needs arise because of differences in sex, age, flexibility, body type and size, etc.

Prior art systems did not advise the student of these nuances. Rather these prior art video systems merely presented the bio-technical data and leave it up to the student or personal instructor to interpret the results. Thus, for example, prior art videotapes could universally present the proper stance and posture; however, they could not customize the videotape to verbally tell the student the faults with his stance and posture and demonstrate and explain why that positioning was inferior to the proper position for that student's characteristics. These prior art systems ignored that no one stance and posture is correct for all golfers. Their approach to golf is no different than would be a doctor who blindly diagnosed a person with certain blood pressure or cholesterol results without knowing other factors about the patient. Additionally, many systems simply provide the data and leave it up to the instructor or student to interpret the data. For example, can a patient interpret a blood pressure reading of 140 over 100 without a doctor or medical book.

Thus, rather than providing a precise geometrical or statistical analysis of a golfer's swing, as accomplished by the systems described above, it is preferable to customize the videotape to teach students which aspects of swing position are fundamentally important to the student's own swing and which aspects are merely matters of personal style. Furthermore, the instruction should account for the student's own particular body type, physical characteristics, and handicaps. Traditionally, as did some prior art systems, an instructor explained the basic fundamentals of a good swing while the student and instructor review the student's videotaped swing in order to interpret the results. However, such personalized instruction is expensive and time consuming, and thus inaccessible to a large portion of the general public and to large groups at one time. Equally important is that the quality of the lesson depended on instructor's ability, disposition at the time of the individual lesson and equipment available to document the lesson.

Inspirational value of personalized instruction is more subjective but undeniably important. To watch and listen to an acknowledged master or admired role model can often motivate physical feats where lessons or practice frequently fail. However, few if any students ever have the opportunity to receive personal coaching from such an instructor. Even if the student could afford to purchase such instruction, there is simply not enough masters and role models to go provide personalized instruction to all who could benefit.

Thus, a system is needed in which a professional instructor or athlete provides training on the basic fundamentals of a good swing that varies from student to student depending on that student's needs and characteristics. A recognized inspirational professional would provide uniformly superior instruction that would be unvarying for day to day, week to week. In such a system, for example, a professional's swing could be shown next to the student's swing to help students understand the fundamentals. However, both the professional's swing and verbal instructions would depend on the individual student's characteristics. The system should be available to a mass population of golfers, and to large number of golfers at a time, and should provide the instruction in a form which allows students to carefully and repeatedly review the instruction at their own leisure and in the convenience of their own homes using standard commercially available videotape or other commonly available electronic equipment.

To be economical any system should reduce to the minimum the need for human participation in the customization of the lesson to the student's characteristics. To handle large groups of students, for example, 200 golfers during a typical 6 hour tournament, the system should be able to produce large quantities of personalized tapes in a short period of time. To minimize the amount of production equipment the system should spend relatively short periods producing each videotape, in recording the student golfer's swing, analyzing that swing, and creating the videotape lesson.

However, past systems that produced golf instruction videotapes have not been able to sufficiently tailor the instruction to provide instruction on the same level as a personal instructor without extensive human involvement. They lacked automation that permitted high quality, professional personalized video instruction. These systems effectively eliminated the personalized instruction. In effect, they offered one lesson for all. Alternatively, the prior art employed personal human instructors with the attendant disadvantages: high cost, inconsistent quality, varying ability, limited availability, inadequate product yield, and lots of time needed to produce 200 tapes.

Moreover, the system should not necessarily be restricted to videotapes. Other systems are presently available, including CD-ROM and video disk, and more will undoubtedly will soon at hand that can present to a student golfer video and audio instruction. Any system should be adaptable to these other media.

The present invention provides such a system and solves these and other problems associated with existing golf video systems.

SUMMARY OF THE INVENTION

It is an object of the present invention to solve the problems described above associated with existing golf video systems.

It is another object of the present invention to help golf players improve their skills.

It is another object of the present invention to allow golf students to view their golf swing and compare it to a professional's swing while receiving instruction from a professional instructor on the basic fundamentals of a golf swing.

It is another object of the present invention to provide a personalized golf instruction video that is tailored to the individual characteristics of the student golfer and which is relatively inexpensive and compatible with most standard commercially available videotape players, CD-ROM, other commonly available electronic equipment.

It is another object of the present invention to automatically edit a partially prerecorded standard videotape by inserting additional full motion video, audio, graphics, or still frames in predetermined locations on the tape.

It is another object of this invention to automatically tailor an instructional videotape for a student golfer through a programmed computer selecting and constructing video inserts for a partially pre-recorded video tape based upon stored information relating to the student golfer.

Some or all of the above and other objects of the present invention are achieved by a system for producing a personal golf lesson video comprising one or more cameras for recording a person's golf swing, capture and memory means connected to the one or more cameras for capturing and storing the recorded golf swing, selection means connected to the capture and memory means for selecting at least one portion of the recorded golf swing, a partially prerecorded golf lesson videotape having gaps in predetermined locations, and a video cassette recording device for copying the selected at least one portion of the recorded golf swing into the gaps of the prerecorded videotape golf lesson.

The partially prerecorded videotape contains a golf lesson given by a professional instructor explaining various aspects regarding the fundamentals of a good golf swing, including factors such as proper positioning and weight distribution. Time codes are recorded in the gaps in the tape to help the VCR locate the gaps under the control of a computer.

In accordance with the invention, a method comprises producing a personal golf lesson videotape from a visual recording of a person's golf swing and a partially prerecorded golf lesson videotape including the step of recording into a computer file in a computer near the golf tee a student golfer's swing. A second computer file is created that contains information about said person, at least some of which relates to the characteristics of the person's swing. Both first and second computer files are moved from the computer in the vicinity of the golf tee to a second computer.

In the second computer an operator selects from the first computer file those frames which most closely match predetermined positions in the golf swing and records in the second computer file in the second computer additional information, at least some of which relates to the characteristics of the person's swing and body positions. A computer selects segments from the instructional video and audio segments based upon information in the second computer file and combines the selected instructional video and audio segments with at least one of the selected frames into a series of video frames. The series of video frames and audio are then inserted into a gap in the partially pre-recorded videotape.

Additional content such as video or still frames of the professional's swing or additional audio information such as verbal instructions from the professional may be inserted into the gaps along with the video or still frames of the recorded golf swing. The professional's and golfer's video or still frames may be placed in a split screen, side-by-side fashion in the gaps. The pace of the full motion visual recording of the person's golf swing is preferably adjusted to substantially match the pace of the fall motion recording of the professional's golf swing.

In accordance with another aspect of the present invention based upon the information in the second computer file a computer dynamically generates a sequence of computer instructions to select at least one segment from the instructional video segments and at least one of the selected frames of the student golfer. Further using the sequence of dynamically created computer instructions the computer constructs a series of video frames to insert into the gap in the prerecorded instructional videotape that are personalized to the student golfer.

BRIEF DESCRIPTION OF THE DRAWINGS

The invention is illustrated in the figures of the accompanying drawings which are meant to be exemplary and not limiting, in which like references refer to like or corresponding parts, and in which:

FIG. 15 is flow chart showing the steps performed at the trailer unit shown in FIG. 9;

FIG. 16 is flow chart showing the processes of generating a script file to create an insert for a gap of the tape shown in FIG. 1;

FIG. 17 is a portion of template code used to generate script file in accordance with the flow chart of FIG. 13.

FIG. 18 is a shot showing a split screen with the instructor illustrating the same swing position as the student.

DETAILED DESCRIPTION OF THE PREFERRED EMBODIMENTS

Figure 1:
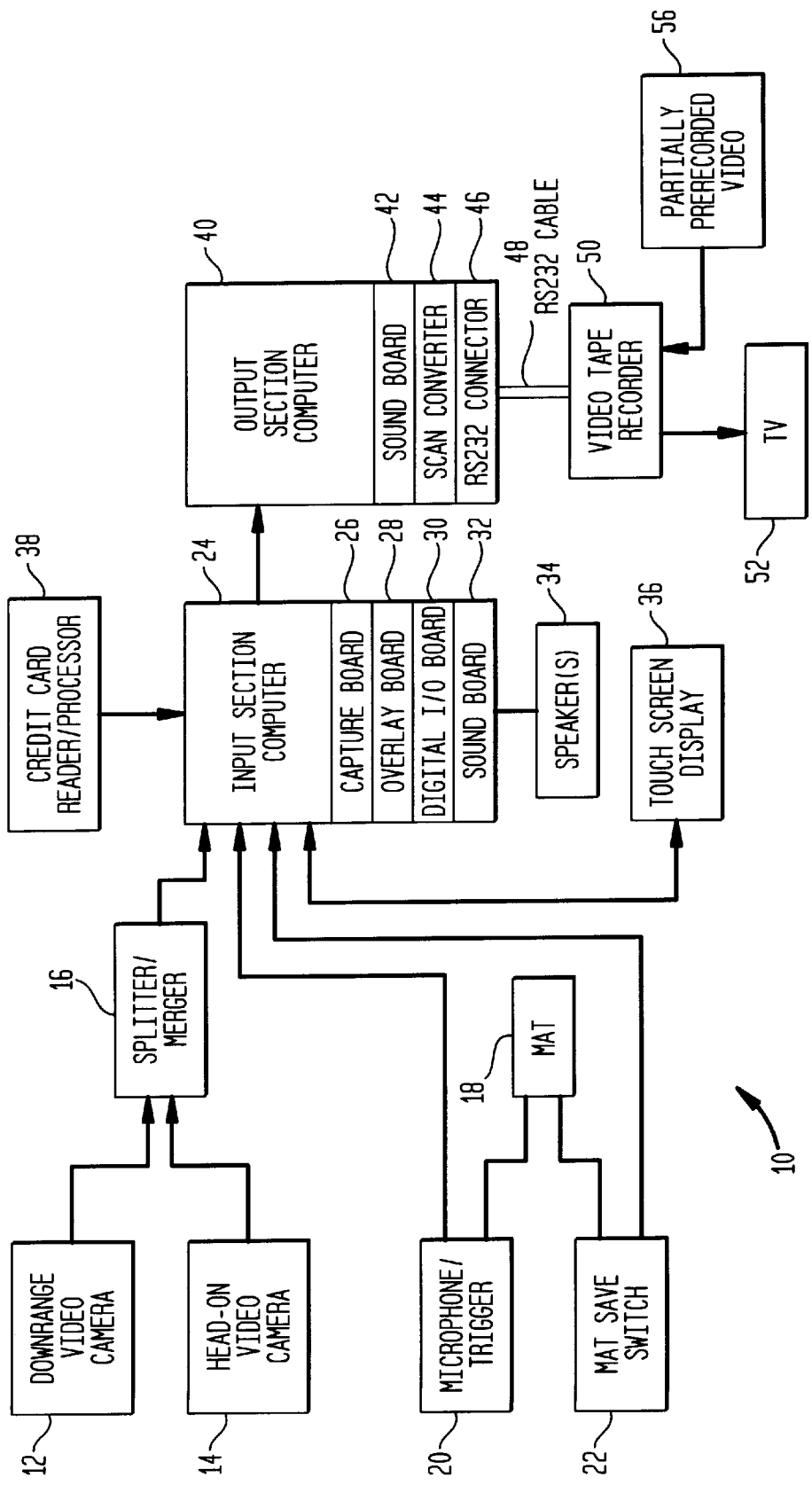
FIG. 1 is a schematic representation of the videotape having gaps in accordance with the present invention.

Shown in FIG. 1 is a schematic representation of a videotape 1 according to the present invention. Video tape 1 has a series of prerecorded segments 3 and gaps 5, 7, 9, and 11, as will become evident from the description below. Into each of the gaps 5, 7, 9 and 11 is inserted the video and audio segments customized for the particular student golfer for which the instructional video 1 is produced.

The invention accomplishes the objectives of creating a high quality instructional golf videotape customized to reflect the individual golfer's characteristics that is economically feasible. To achieve these goals the invention utilizes a plurality of partially pre-recorded videotapes, each of which is personalized to a large group of golfers (e.g., left handed, right handed, seniors, women), that save additional time during the actual recording of the final videotape. A menu and graphically driven editing process permits an operator in short order to select key frames in the video of the student golfer's swing and to characterize the swing's attributes. During the production of the videotape, during the taping and subsequent key framing, particular characteristics of the student golfer are recorded into computer files and subsequently enable a computer to dynamically create computer instruction that insert video and audio segments into the gaps in the partially pre-recorded videotape.

These insertions can be dynamically created during the interval when the partially pre-recorded videotape is advanced from one gap to the next. Thus creating the customized video and audio insertions adds no actual production time to creating the finished videotape. The present invention uses dynamically created split screen comparisons of the instructor and the student golfer. It also dynamically creates graphics, such as telestrations, that are superposed into a video frame or frames.

The present invention is now described with reference to the accompanying drawings. The invention uses a plurality of prerecorded videotapes 1. In one embodiment there are prerecorded videotapes for males, females, and senior golfers. In addition there is a basic lesson, a comparison lesson, and a follow up lesson. Additionally, for each of the foregoing tapes there is a version for left handed golfers, and another version for right handed golfers. One skilled in the art will readily imagine other types of lessons and variations on golfers that can be used to make a variety of lessons. Furthermore, in accordance with the present invention some of these prerecorded videotapes could be eliminated and replaced by dynamically creating each variation from one or more basic prerecorded videotapes and larger selection of prerecorded video segments.

Figure 13:
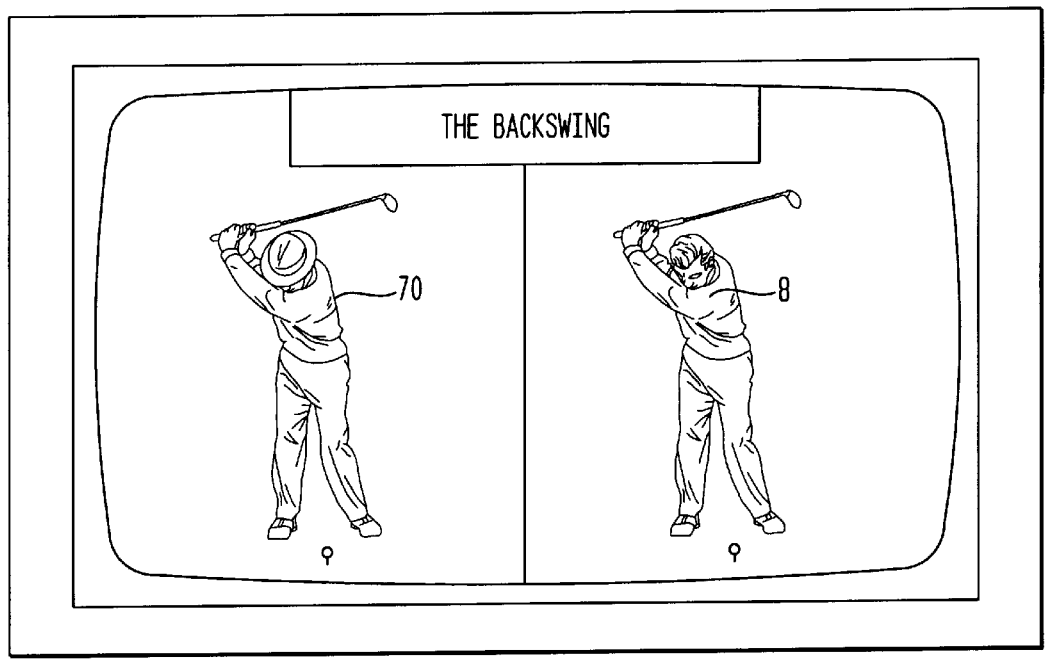
FIG. 13 is a shot of the edit screen on the monitor shown in FIG. 9.
Figure 14:
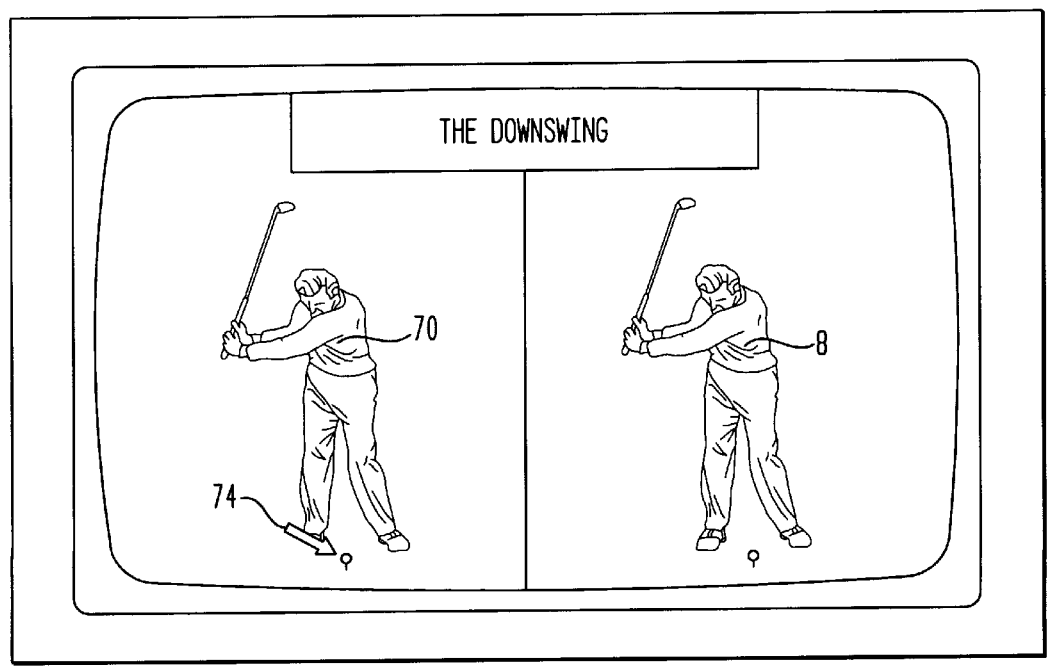
FIG. 14 is a shot of the output screen on the monitor shown in FIG. 9.

Each of the partially prerecorded golf lesson videotapes contains a lesson on the fundamentals of a good golf swing that a professional instructor teaches. The instructor explains the basic techniques, including proper body position, weight distribution, club positioning, alignment, and the general "feel" of a good swing. As shown in FIG. 13, fundamentals may be listed in checklist form on the screen.

On videotape 1 the professional helps to illustrate the fundamentals with an example swing, which is shown in full motion video as well as in still frames. Other techniques well known in the art, such as telestrations, graphic lines superimposed over the golfer, and still frames of the instructor's swing at critical positions, are further provided to assist the student in his/her understanding.

For example, the instructor's swing can be inserted in a side-by-side relationship with the golfer's swing, and still frames of the instructor's swing at various positions, such as the set up, the back swing, the down swing, the follow-through, etc., can be inserted in a side-by-side relationship with still frames of the golfer's swing shown in the corresponding position. See FIG. 18, representing a screen shown in the final, edited version of the personalized golf lesson videotape in which a still frame of the instructor 70 is shown side-by-side with the golfer 8. Additional audio information, such as the instructor's verbal explanations, can also be inserted in the gap. Also, telestration effects may be added, as shown by the lines 74 in FIG. 13, to further assist in teaching the fundamentals regarding proper positioning.

The computer set up at the tee unit has one main computer and one drone computer. The main computer runs the application and also captures video. The drone computer captures just the video. The two computers are linked through together through an ordinary computer ether network.

As more fully described below according to the present invention for each golfer for which a video is made an operator enters certain information into a configuration file. For example, the golfer's name, his particular category (male, female, or senior), and the type of lesson (basic, follow up, and swing plane). Although this preferred embodiment uses an ordinary ASCII text file, a person skilled in the art will recognize that other computer file formats for the configuration file can also be used with no loss in functionality.

Figure 2:
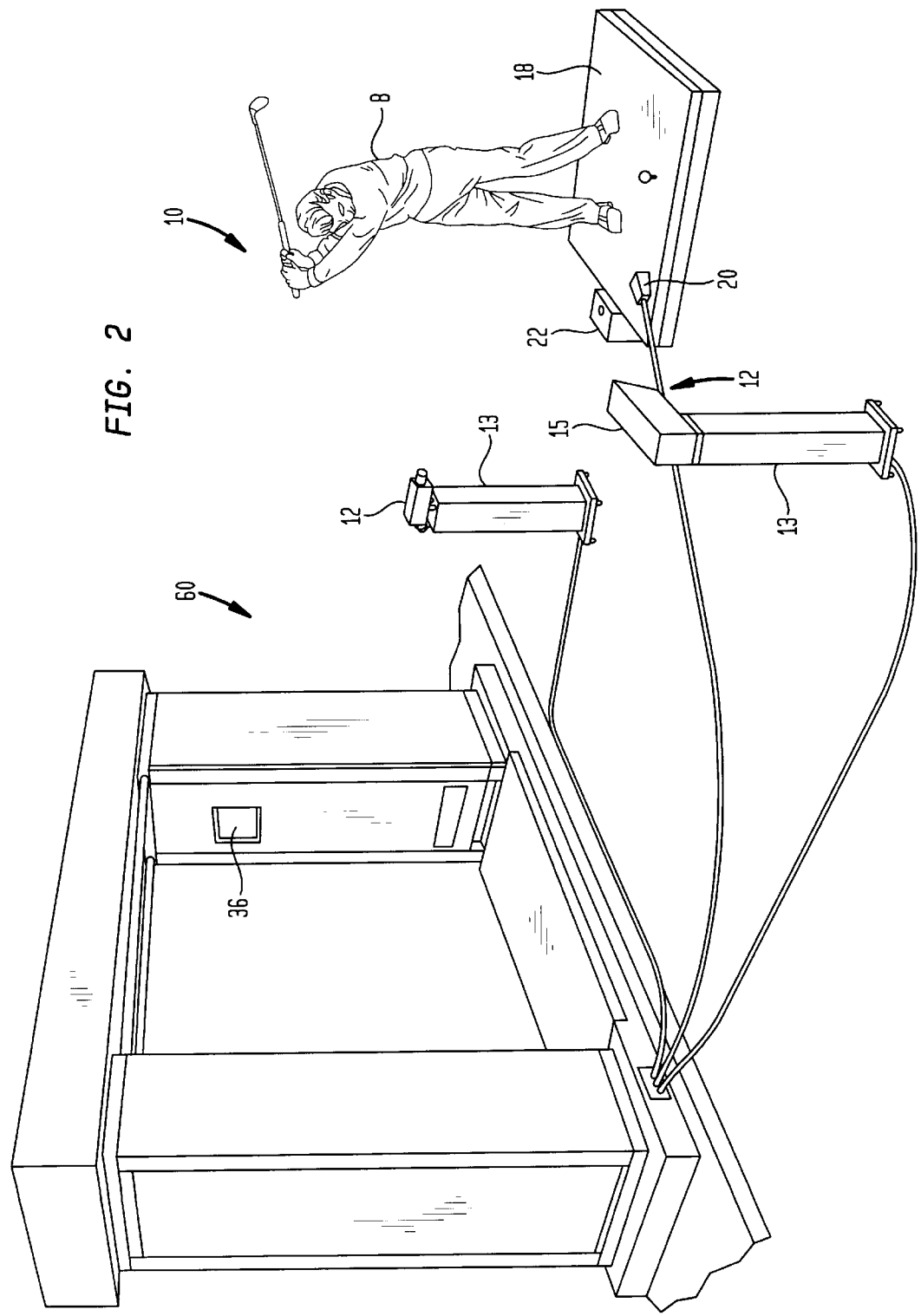
FIG. 2 is a perspective view of the tee unit of the present invention comprising video cameras and a tee cabinet.
Figure 8:
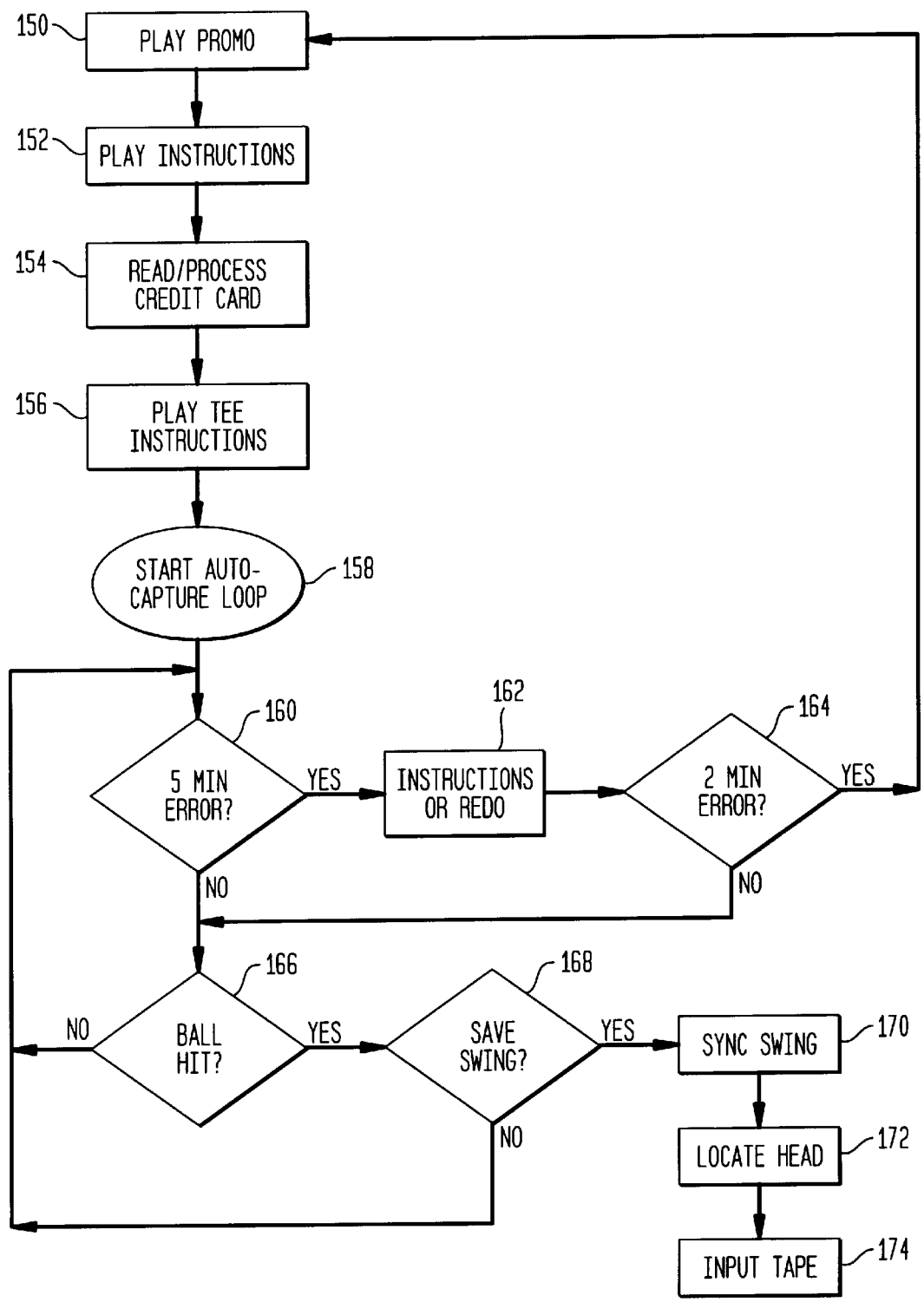
FIG. 8 is a top plan view of the trailer unit of the preferred embodiment of the present invention.

In the preferred embodiment, there is both the tee unit 500 and the trailer or central unit 601 (FIG. 8). The tee unit 500 and its parts are set up are shown in FIGS. 2 through 7. FIG. 2 shows a perspective view of tee unit 500 of this embodiment.

The unit 500 comprises three video cameras, 501, 503 and 505. Video camera 501 is the front view right camera, video camera 503 is the down range camera, and video camera 505 is the front view left camera. For a right-handed golfer, the front view right camera 501 and the downrange camera 503 are employed. On the other hand, for a left handed golfer, the front view left camera 505 and the downrange camera 503 are used.

Figure 3:
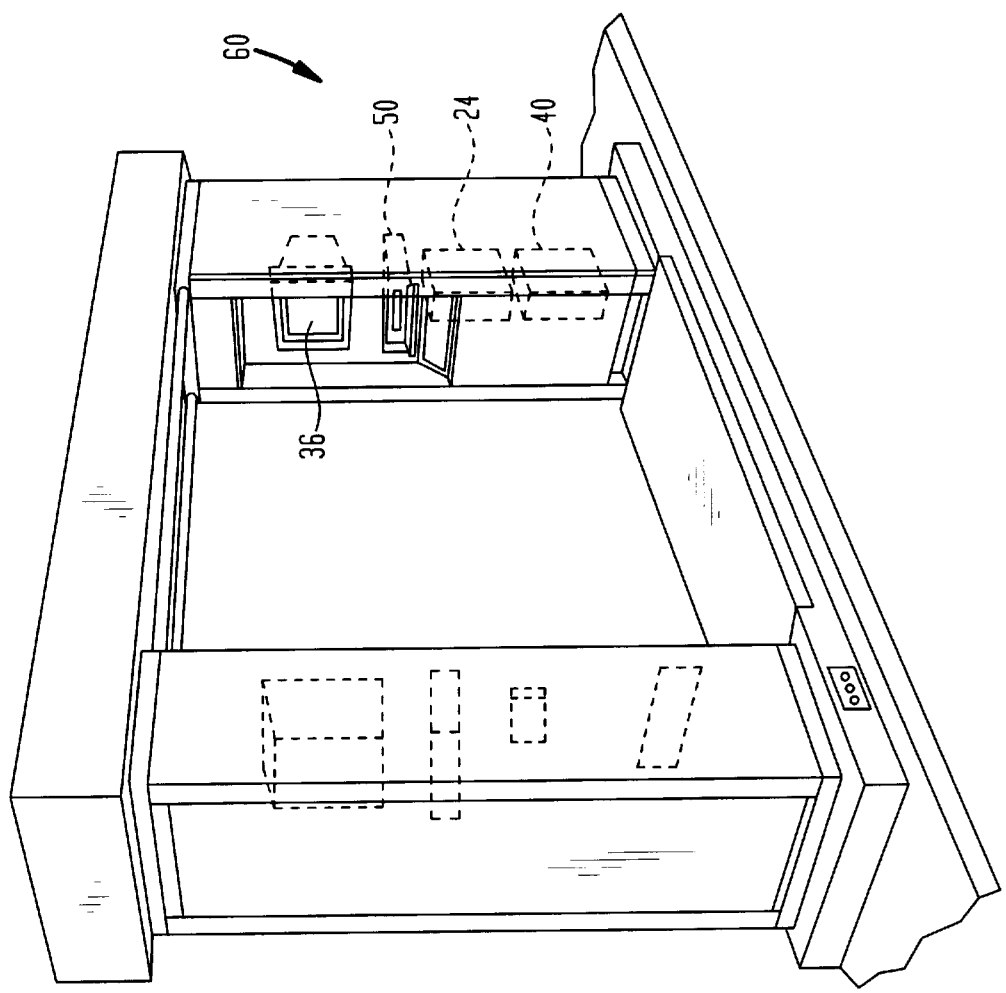
FIG. 3 is a side view of the tee cabinet shown in FIG. 2.

As shown in FIG. 3, golfer 8 stands at tee 507. The video outputs of each of the video cameras 501, 503, and 505 are fed into the console 509. The console 509 preferably comprises at least two computers, as is more fully described below. Also evident from FIG. 2 in tee console 509 is monitor 511 and keyboard 513.

Figure 5:
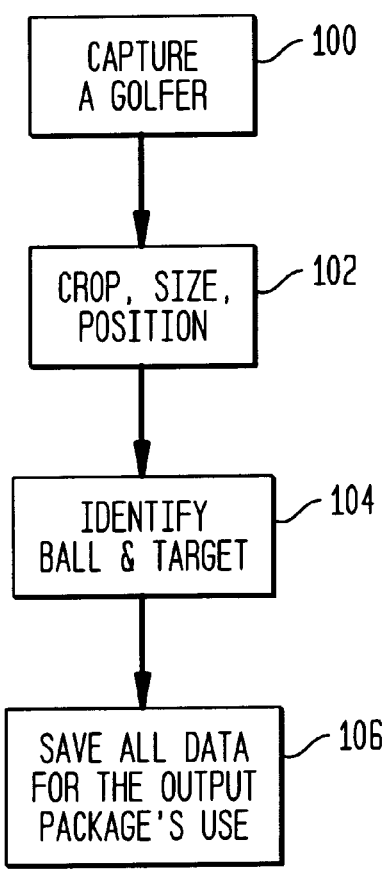
FIG. 5 is schematic representation of the video signal flow in the tee unit shown in FIG. 2.

Shown in more detail in FIG. 3 is tee console 509. In addition to monitor 511 and keyboard 513 there are two computers: main computer 515 and drone computer 517. In the preferred embodiment an additional computer 519 is also provided as a backup to both the main computer 515 and drone computer 517. FIGS. 3 and 5 also illustrate a black burst box 521, a camera power supply 523, an A/B switcher 525, a router switcher 527, a router switch 529, a power switch 531, and camera connections 533. As one skilled in the art recognizes burst box 521 synchronizes the video frames that cameras 501, 503, and 505 produced.

Figure 4:
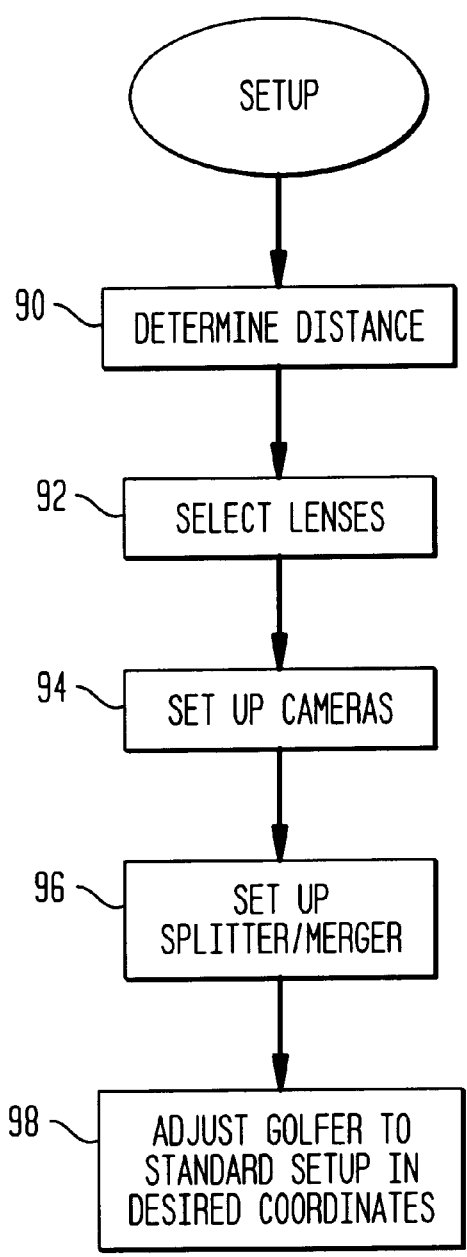
FIG. 4 is front view of the cable connectors in the tee cabinet shown in FIG. 3.

Referring now to FIG. 4, a more detailed illustration appears of the camera connections in console 509. Camera connections 535, 537, and 539 are provided respectively for the front view right camera 501, the down range camera 503, and the front view left camera 505.

FIG. 5 illustrates the wiring of console 509. The output from down range camera 503 is connected to terminal 535 on camera connections 543. From there it is fed directly to the input 541 of drone computer 517. On the other hand, the outputs from front view right camera 501 and front view left camera 505 are fed through the respective connectors on camera connections 533 to a router switch 527. Under operator control switch 527 directs the appropriate video output, depending on whether it is a left handed golfer or a right handed golfer, to the video input of a video capture board 543 in main computer 515. In the preferred embodiment an Azeena video capture board, manufactured by Azeena Technologies, P.O. Box 92169, Long Beach, Calif. 90809, is used.

The video analog output of the video capture board 543 is fed to the input of a video overlay board 547. Overlay board 547 combines the video signal with the ordinary VGA video from computer 515 to allow both the computer and camera video to appear simultaneously on monitor 551. The Hauppauge overlay digital video board, manufactured by Hauppauge Computer Works, Inc., 91 Cabot Court, Hauppauge, N.Y. 11788, is the overlay board that is used in the preferred embodiment. The manufacturer of overlay board 547 provides a special loop connector that connects the overlay board to both the output of the VGA video card 545 and the input to the VGA monitor 511. Overlay board 547 merges the video signal from one of cameras 501, 503, and 505 into a window that is created in VGA monitor 511. Accordingly, FIG. 5 shows a connection between the overlay board 547, the VGA video card 545, and monitor 511.

Similarly, the analog video output of the video capture card 543 of drone computer 517 is routed to the input on router switcher 527. Under control of the operator at tee unit 500 video router switcher 527 can route that input to the input of the overlay card 547 on main computer 515, thusly making available in the window on monitor 511 an image from the downrange video camera 503.

Also in this embodiment is a PC keyboard encoder card 549 that converts an electronic pulse into an IBM PC compatible key code. Connected as inputs to the encoder card 549 are keyboard 513 and capture switch 529, the function of which is described immediately below. The preferred embodiment uses the KE24 PC Keyboard Encoder of Hagstrom Electronics, 2 Green Lantern Boulevard, Endicott, N.Y.

The output of encoder card 549 forms the input both to keyboard input 551 of the main computer 515 and keyboard input 553 of drone computer 517. Capture switch 529 is connected to input of encoder card 549. Upon closure of capture switch 529 encoder card 549 produces the key code for the escape key, which code is simultaneously sent to the keyboard inputs of both main computer 515 and drone computer 517. Thus both main computer 515 and drone computer 517 simultaneously receive a signal that stops computer 515 and 517 capturing video from cameras 501–505.

As known to those skilled in the art, main computer 515 contains programs that perform all supervisory functions for both computers 515 and 517. Main computer 515 controls and communicates with drone computer 517 through a conventional computer network using typical ethernet network cards.

Main computer 515 also provides a user interface for the operator on monitor 511. Main computer 515 records either front view right camera 501 or front view left camera 505 into its main memory and hard disk. Drone computer 517 records into its memory and hard disk the video from downrange view camera 503.

In the preferred embodiment main computer 515 is also provided with a removal high capacity storage media 555 (see FIG. 3). The preferred embodiment uses an Iomega SCSI JAZ 1-gigabyte disk. Removal high capacity storage media 555 transports the video and configuration files from tee unit 500 to trailer unit 601 as is evident from the description below. Of course, one skilled in the art could substitute other means to move the files from the tee unit 500 to the trailer unit 601 including read write CD-ROM's, streaming tapes, or network communications.

Backup computer 519 provides a spare for either main computer 515 or drone computer 517 in the event that one of two computers 515 or 517 fail. By having a spare computer available, the preferred embodiment suffers no downtime in the event of a computer failure in tee console 509 to permit golf lessons continue unimpeded.

Figure 6:
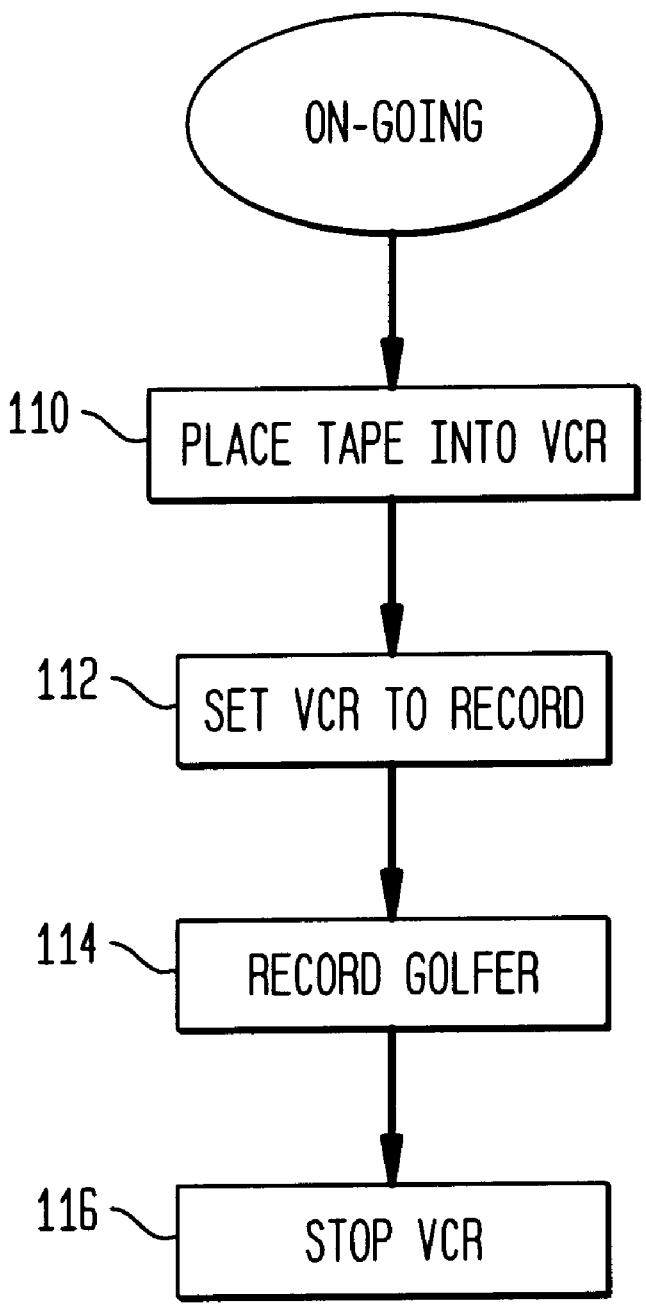
FIG. 6 is a screen shot of the monitor in the tee cabinet shown in FIG. 3.
Figure 7:
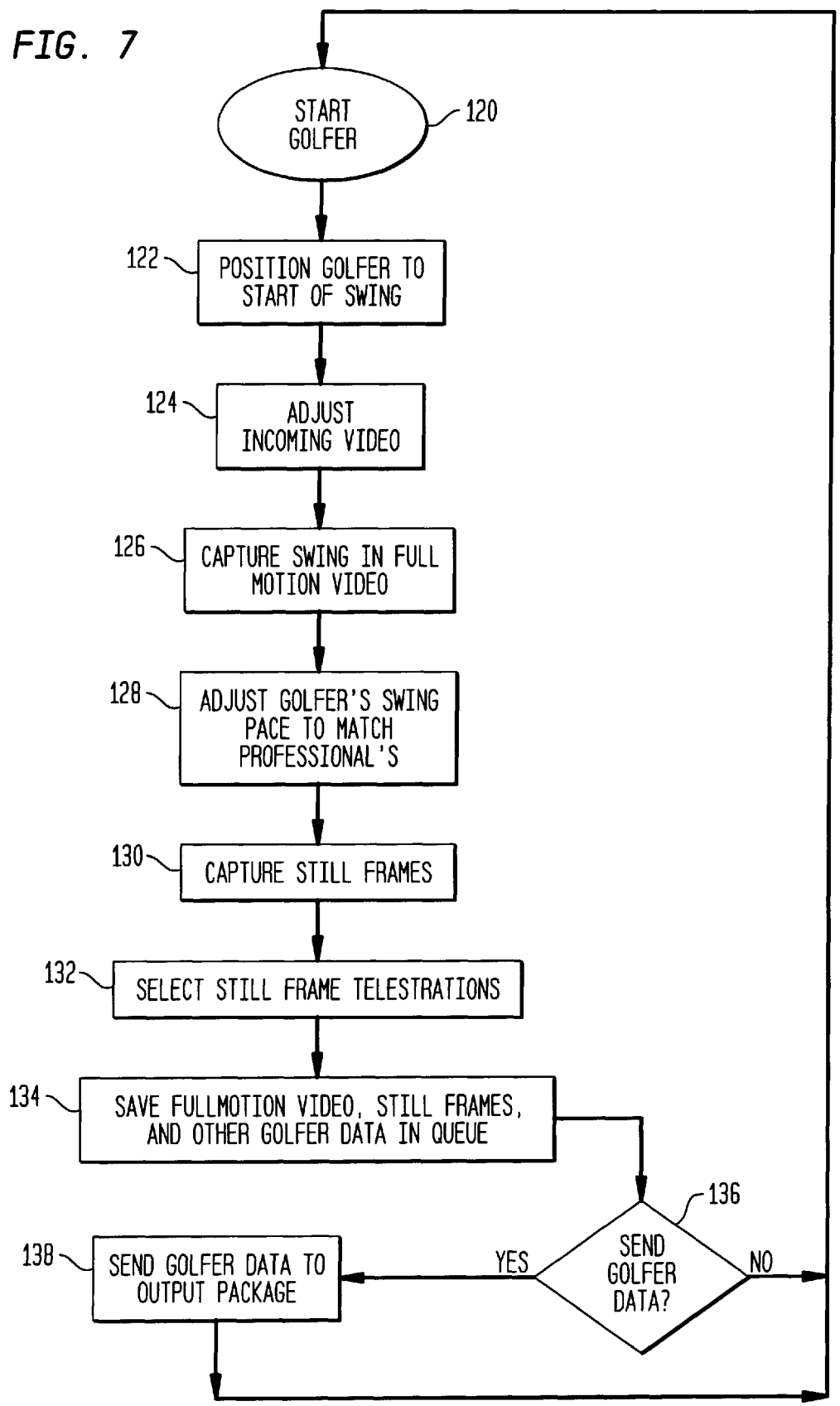
FIG. 7 is flow chart showing the processes of recording a golfer's swing at the tee unit shown in FIG. 2.

Shown in FIG. 6 is the user interface for the operator that is displayed on monitor 511 during use of tee console 509. In practice, the tee unit shown in FIGS. 2 through 6 is used as follows. The operator directs the student golfer to the appropriate side of the tee as shown in FIG. 2 and selects the appropriate camera as shown in step 575 in FIG. 7. At step 577 the operator enters the data that characterizes the student golfer including: name, accession, description that most typifies the student golfer's swing type, and other information shown in FIG. 6. In the preferred embodiment, as previously described 3 types of swings are categorized: leverage, arc and width.

Having done the foregoing, the operator clicks on "add to list" button. At step 579, the operator then clicks on Monitor 511 on the "capture a golfer" button and on the golfer's name whose swing is about to be captured.

At this point, computers 515 and 517 enter capture mode. Each computer records continuously the output of its associated video camera. Computers 515 and 517 store the frames captured off cameras 501 and 503 in a circular buffer in their respective memories. In the preferred embodiment, this buffer is sufficiently large to hold 3 seconds of a golfer's swing. At 30 frames a second the buffer thus holds 90 frames. At the end of that period the computer records newly received frames in the same memory locations where previously recorded frames were stored.

The operator then instructs the golfer to take his swing. After a satisfactory number of practice swings, and upon a swing that typifies the golfer's swing, as illustrated at step 581, the operator pushes the stop capture button 529.

Other means to stop the capture also are readily available. For example, a microphone could be cued to detect the impact of the club with the ball and thereafter cause the recording to stop after the passage of the time necessary for a golfer to complete the swing.

The information for each individual golfer is saved into a particular directory structure. For example, the avi file (front, left or right) and the configuration file are placed into two sub-directories "front" and "list" of the "swings" directory, respectively on main computer 515 and the avi file (down range) on drone computer 517 in a sub-directory called "target" of the "swings" directory.

After succeeding in capturing the swing of the golfer, computers 515 and 517 check to insure that the files were correctly recorded at 583. They compare the actual size of the capture file in memory to that of the estimated size of a three second avi file. If the comparison is not within the pre-determined tolerance, an error is indicated and the operator will repeat the capture procedure. In the preferred embodiment, each avi file is approximately 3.4 megabits.

Main computer 515 transfers all files for a particular golfer to the removable media, in the preferred embodiment JAZ disk 555. On each JAZ disk three sub-directories of the "swings" directory are created: "front", "list", and "target."

The preferred embodiment of the invention also has a trailer unit 601 as shown in FIG. 8. Trailer unit 601 comprises a trailer 603. In the preferred embodiment, trailer 603 is sufficiently large to house not only all the equipment necessary to produce customized videotapes of student golfers, but also sufficiently large to transport at least two tee consoles 509, shown in dotted lines in FIG. 20. During normal operation of trailer unit 601, tee consoles 509 are removed from trailer 603 and are deployed in the field. Permitting entry into trailer 603 is door 605.

Trailer 603 permits the mass production of instructional videotapes at or near the site on a "real time" basis for almost immediate delivery where the swing of the student golfer is captured. Trailer 603's and its equipment's close proximity to the student golfer, described below, permits the rapid production of finished videotapes.

Trailer 603 also has AC generator 607 and alternate AC generator 609. These generators provide mobile power when AC power is not available. In the preferred embodiment, trailer 601 is also adapted to accept outside power through hatches in the front of trailer 603.

In addition to various storage cabinets and videotape dispensers, collectively numbered 611, trailer 603 also contains console 613. Console 613 is shown in more detail in FIG. 9.

Trailer 601 has 8 computers: one input computer 615, and seven output computers 617, 619, 621, 623, 625, 627 and 629. Associated with each of the output computers 617 through 629, is a video cassette recorder ("VCR") 631, 633, 635, 637, 639, 641 and 643. Input computer 615 also has a high capacity removable media drive 645, such as the aforementioned Iomega JAZ drive. Input computer 615 is networked to the other output computers 617 through 629 through network hub 661. All of the computers are IBM compatible computers with Pentium 100's and 32 Megs of RAM and at least 1.3 gigabyte hard drive. For reliability and ease of mounting, PC Bus Industrial Computer rack mountable cases are used for the PC's.

Figure 9A:
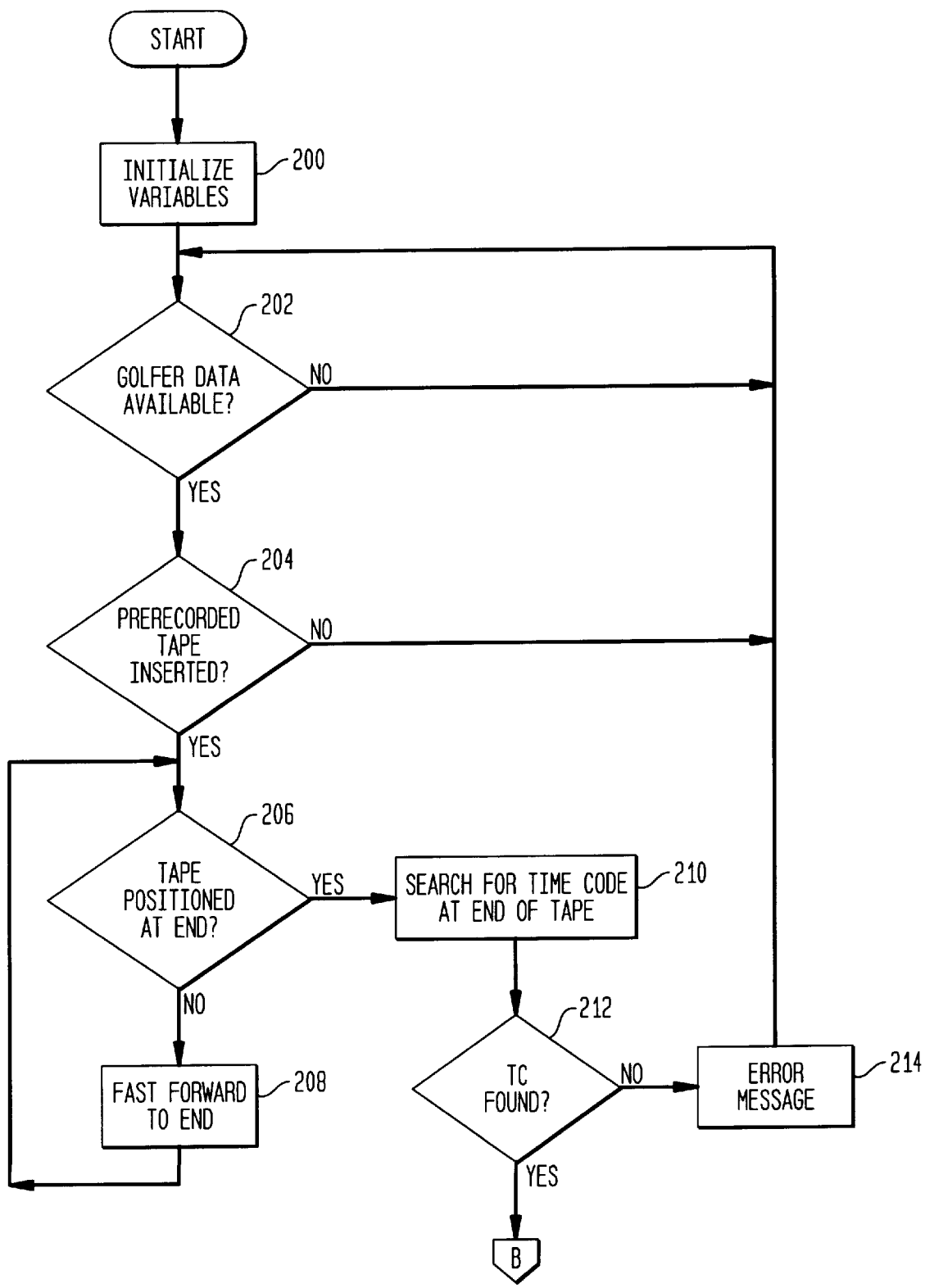
FIG. 9 is a front view of the cabinet in the trailer unit shown in FIG. 8.
Figure 9B:
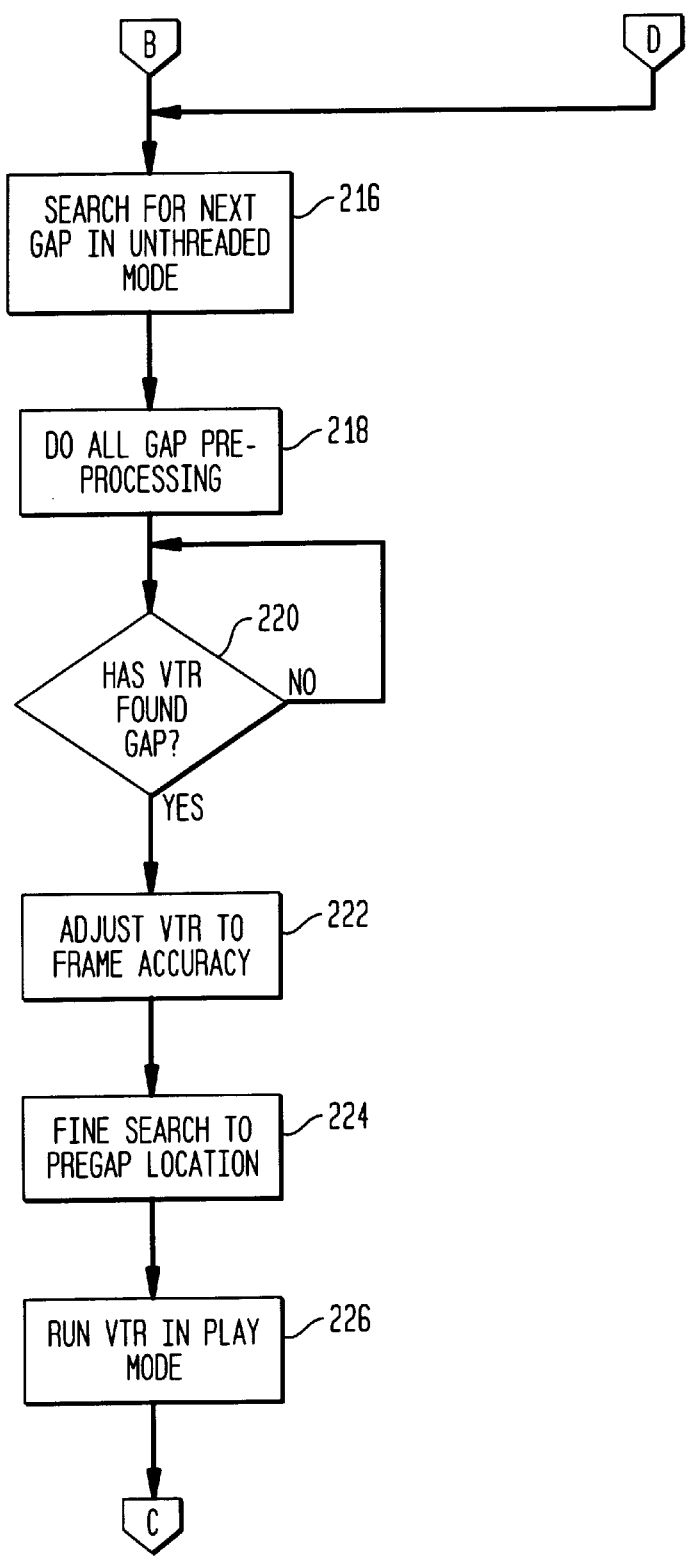
Figure 9C:
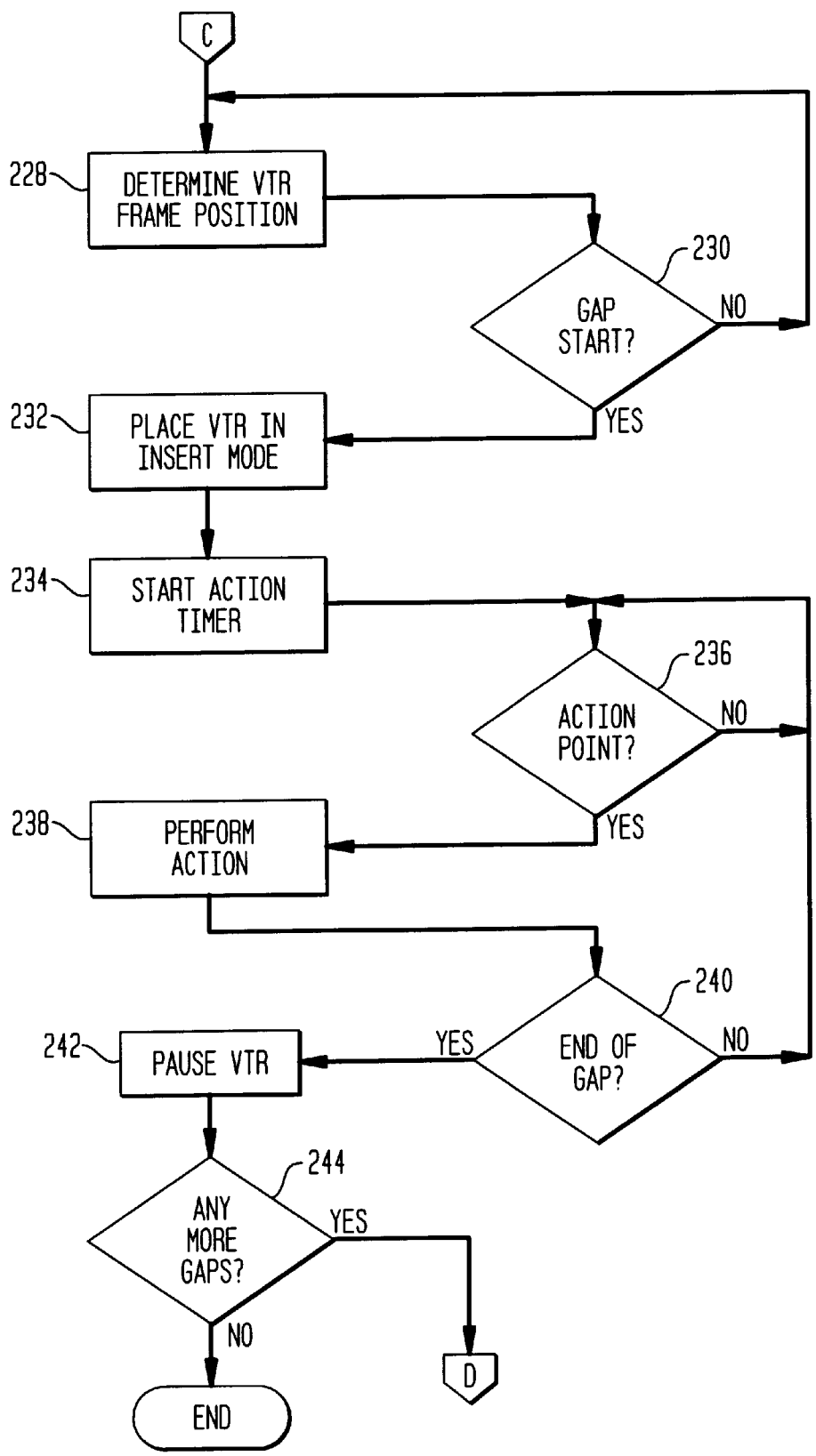

Also shown in FIG. 9, console 613 also has a conventional VGA monitor 653 and a conventional analog television monitor 655. Also shown in FIG. 9 is a mouse 657, label printer 659 and network hub 661. The preferred embodiment also provides a backup computer 663 in the event any of the other computers fail.

Sitting on the top surface of console 613 are scan converters 665, 667, 669, 671, 673, 675, 677, each of which is associated with one pair of output computers 617 through 629 and VCR's 631 through 643. Each scan converters converts the VGA signal output from one of computers 617 through 629 to NTSC video, which the VCR accepts and records onto the partially pre-recorded videotape 1. The preferred embodiment uses Extron Electronics Super Emotia scan converters that Extron Electronics/RGB Systems, Inc., 1230 South Lewis Street, Anaheim, Calif. 92805, manufactures.

Figure 10:
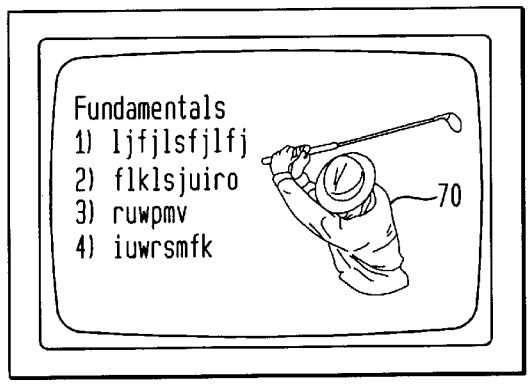
FIG. 10 is schematic representation of the video signal flow in the trailer unit shown in FIG. 9.

FIG. 10 illustrates the video signal flow in the preferred embodiment of the trailer unit 601. This FIG. 10 shows the signal flow for one output computer with its associated VCR and scan converter. Also shown is input computer 615 and its network connections to the output computers 617.

Forming inputs to input computer 615 are keyboard 658 and mouse 657. Electronic selector box 649 is an intelligent electronics switch that switches all of the computers to one keyboard, monitor and mouse. The preferred embodiment uses a switch from Rose Electronics, 10707 Stancliff Road, Houston, Tex. 77099.

Thus, monitor 653, mouse 657 and keyboard 658 are connected to the appropriate terminal on electronic selector box 649. Similarly, a port on the box 649 is connected to computer keyboard and mouse input connectors, on one of output computers 617 through 629, as well as the monitor output connector on one of the scan converters associated with that particular output computer. Electronic selector box 649 is also connected to the VGA board, mouse connector and keyboard connector on the input computer 615.

Each output computer 617 through 629 has its VGA board's output connected to the CPU port on its associated scan converter 665–677. Similarly, each output computer 617 through 629 is connected through its network board to a port on network hub 661. The output computer also uses a sound multimedia card whose output feeds into the audio input on the VCR associated with the respective computer.

The video input on TV monitor 655 is connected to the video output on the selector box 650. And the audio input on TV monitor 655 is connected to the audio output on the selector box 650. Switch box 650 selects the video and audio output of each of one of VCR 631–643 to the input of TV monitor 655.

The editing process that occurs in trailer unit 601 is explained in conjunction with FIGS. 11 through 15. FIGS. 11–14 are screen shots of the operator interface that appears on VGA monitor 653. The operator begins the editing process by placing into removable media disk drive 645 the removable media that contained the student golfer's video and configuration files that had been produced at tee unit 500. The operator clicks on the JAZ button shown on the interface in FIG. 11. Golfers' names will fall into one of three categories. The raw category is where no editing has been done to the golfer's swing. For those golfers listed in the key framed category, the operator has already key framed his or her swing. The golfers contained in the edited list have been both key framed and edited, as those terms are described below.

Computer 615 must synchronize the student's golfer's swing to with that of the instructor. In the preferred embodiment the instructor's swing comprises 32 frames. Of these the preferred embodiment uses 8 key positions—set up, take away, mid-back, top, down, impact, follow-through, and finish—the computer lines up with the identical points in the instructor's and students swing. If the number of frames in between the two points differs between the teacher's swing and that of the student golfer, the computer subtracts or duplicates and adds frames in the golfer's swing. Through this process, the student golfer's swing is synchronized; e.g., interpolated, to match that of the golf teacher.

To key frame a particular golfer, the operator clicks on the golfer's name in the raw list. The particular golfer appears on monitor 653 in the screen shot shown in FIG. 12. The operator first must select the correct "set up" position. This is the frame where the club head begins the backward motion of the swing. The operator may move the video clip frame by frame either backwards or forwards by clicking the appropriate button.

The present invention maximizes the probability that an ideal key frame for the particular stroke position is selected. As previously noted the preferred embodiment of the present invention captures 3 seconds of golf swing at 30 frames per second, or a total of 90 frames. Each frame consists of two fields. Thus the present invention captures 180 consecutive "pictures" of the golf swing. During key framing the operator may select any of those 180 "pictures", thus for example maximizing the operator's opportunity to select the exact moment that the club strikes the golf ball.

When the correct frame appears on monitor 653, the operator clicks the "accept" button. The operator must select the other 8 positions to complete the key frame selection process. Thus, the operator next selects the take away position. This is where the club head has advanced eighteen inches away from the ball. The operator subsequently selects the remaining positions: mid-back position, where the golfers hands are even with the wrist; the top position, where the club head begins to reverse directions; the downswing position, where the golfers hands are midway between the golfers belt and the shoulders; in mid-down position where the shaft of the club is parallel or as close to parallel as possible to the ground; the impact position, where the club head first contacts the ball; the follow through position; where the club is three to four feet past the impact position; and the finish position, where the golfer has completely finished the swing motion. The operator can then review and change any of the selections by clicking on that position on the monitor, making the change, and accepting the change.

In the next editing step, shown in FIG. 13, the operator selects points on the student golfer's body that are needed for further computer analysis or for the telestrations. For example, in the preferred embodiment during one split screen sequence a line is drawn from the head to ball for both the instructor and the student golfer to illustrate the correct alignment. To enable the computers to later generate this line for the student golfer, the operator clicks on the center of the golfer's head, which causes the computer to draw a white circle on the monitor to encompass the golfers head.

As shown in FIG. 13 the computer helps the operator select the proper points by giving the operator sequential numbers. For example, the operator clicks on (1) the ball, (2) the club, (3) the toe, (4) the heel, etc. Assuming that the operator performed the preceding steps properly and to the operator's satisfaction, the operator clicks accept and the program is then set for the operator to indicate through mouse clicks the positions needed for the next telestration.

According to one embodiment, the operator creates the following points:

Head-ball line:
  Click the center of the golfer's head, so the white circle encompasses the golfer's head.
  Click on the ball.
  Click on the point where a vertical line drawn from the ball meets the head circle.
    NOTE: If the vertical line does not meet the head circle, click on a point which is parallel to the middle of the golfer's head.
  Click the "Accept" button to accept and move to the next position that needs telestration. This must be done for every screen.

Front Set Up:
  Click on the target inside heel.
  Click on the back inside heel.
  Click on the middle of the back shoulder.
  Click on the middle of the target shoulder.
  Click the "Accept" button to accept and move to the next position that needs telestration.

Back Set Up:
  Click on the ball.
  Click on the heel of the club.
  Click on the end of the golfer's back toe.
  Click on the middle of the golfer's back ankle.
  Click on the end of the target toe.
  Click on middle of the golfer's knee.
  Click on the middle of the golfer's hands.
  Click on the end of the club shaft.
  Click on the middle of the golfer's thigh, across from dot #7.j.(10) click on the middle of the golfer's hip, usually this will be at the bottom of their pocket.
  Click on the outside of the golfer's back, just below the belt line.
  Click on the outside of the golfer's back, half way up the spine.
  Click on the outside of the golfer's back, just even with the should blades.
  Click on the middle of the target.

Front Take Away:
  Click on the top edge of the back shoulder.
  Click on the top edge of the target shoulder.
  Click on the middle of the target elbow.
  Click on the club shaft where the golfer is holding the club.
  Click on the top of the club where the hozel meets the club head.
  Click the "Accept" button to accept and move to the next position that needs telestration.
Back Take Away:
  Click on the heel of the club.
  Click the "Accept" button to accept and move to the next position that needs telestration.
Front Mid-Back:
  Click on the end of the golfer's target toe.
  Click on the middle of the golfer's back knee.
  Click on the club shaft where the end of the hands is.
  Click on the club shaft as close to the club head as the picture will allow.
  Click on the "Accept" button to accept and move on to the next telestration.
Back Mid-Back:
  Click on the club head.
  Click on point on ground beneath the golfer's feet.
  Click the "Accept" button to accept and move to the next position that needs telestration.
Downswing:
  Click on the middle of the golfer's knee.
  Click on the top of the golfer's forearm, just below the elbow.
  Click on the corner made by the golfer's arm and the shaft of the club.
  Click on the inside of the club shaft, a little lower that the grip of the club.
Impact:
  Click on the golfer's target shoulder.
  Click on the middle of the golfer's elbow.
  Click on the club shaft where the golfer is holding the club.
  Click on the face of the club.
  Click the "Accept" button to accept and move to the next position that needs telestration.
Follow Through:
  Click on the middle of the golfer's back foot.

The present invention is not limited to these points. One skilled in the art readily would recognize other points of comparison that are useful to student golfer to improve his stroke.

Having selected the points, the operator then characterizes the body characteristics and swing types of the student golfer. Although in the preferred embodiment the operator selects from a number of menu and button choices to analyze 15 characteristics, one skilled in the art will readily devise different or additional characteristics to choose. The present invention is not limited to any particular characteristics, but through the use of selected characteristics recorded into a computer file dynamically creates computer instructions to create customized video and audio segments.

The preferred embodiment performs the following steps:
Width Option:
  Depending on the golfer, the operator chooses: "OK", "Too wide", or "Too narrow"

Leverage body type:
  OK: lines intersect through the arm pits
  Too wide: lines are outside armpits
  Too narrow: lines are inside armpits
Arc body type: (same as LEVERAGE)
  OK: lines intersect through the arm pits
  Too wide: lines are outside armpits
  Too narrow: lines are inside armpits
Width body type:
  OK: lines intersect on the outside edge of the shoulders
  Too wide: lines are positioned outside the Width "OK" guideline
  Too Narrow: lines are positioned inside the Width "OK" guideline
Click the "Accept" button after making choice to accept and move to the next option.
Knee Option:
  Choices: "OK", "Too bent", or "Too straight"
  OK: Bend in the knee should be athletic in nature
  Too bent: bend in knee looks awkward and is more in a squatting position
  Too straight: golfer is too upright or knees are in a locked position
Click the "Accept" button after making choice to accept and move to the next option.
Hands Option:
  Choices: "OK", "Too far"
  NOTE: hands position is correct if golfer's hands are a handswidth from body; wrists should not show a large bend up or down.
  OK: golfer's hands are positioned over toes
  Too far: hands are positioned in front of toes
  Too close: hands are positioned over the middle of the golfer's feet
Click the "Accept" button after making choice to accept and move to the next option.
Railroad Option:
  Choices: "OK", "Too closed", or "Too open"
  OK: lines are parallel or slightly converging
  Too closed: lines touch anywhere on the screen
  Too open: lines diverge from one another
Click the "Accept" button after making choice to accept and move to the next option.
Triangle Option:
  Choices: "OK" or "Lost triangle"
  OK: line formed by the left shoulder, hands and club head should be straight
  Lost triangle: line is not straight
  NOTE: The key is the wrist joint.
Click the "Accept" button after making choice to accept and move to the next option.
Club Path Option:
  Choices: "OK", "Too inside" , or "Too outside"
  OK: line intersects with the club head
  Too inside: club head is between the line and the golfer's body
  Too outside: club head is beyond the line
Click the "Accept" button after making choice to accept and move to the next option.
Foot Option:
  Choices: "OK", "Already up", or "Too flat"
  OK: There is a wide range of variation that is considered O.K. here.
  Everything between the too other foot option guidelines is acceptable.

Already up: foot is vertical or on the toe
Too flat: foot is flat on the ground
Click the "Accept" button after making choice to accept and move to the next option.
Head Setup Option:
Choices: "OK", "Too far forward", or "Too far back"
NOTE: Correct choice depends on whether golfer is right or left-handed.
Right-handed golfer:
OK: vertical line meets head circle between 3 o'clock position and 5 o'clock position
Too far forward: line is left of the 5 o'clock head circle position
Too far back: line misses head circle on target side
Left-handed golfer:
OK: vertical line meets head circle between 7 o'clock position and 9 o'clock position
Too far forward: line is left of the 7 o'clock head circle position
Too far back: line is right of the 5 o'clock head circle position
Click the "Accept" button after making choice to accept and move to the next option.
Unwound Option:
Choices: "OK" or "Unwound too soon"
OK: buttons of the golfer's shirt point away from target
Unwound too soon: buttons of golfer's shirt point in front (toward target) of the ball or are facing you
Click the "Accept" button after making choice to accept and move to the next option.
Head Impact Option:
Choices: "OK", "Too far forward", or "Too far back"
OK: golfer's head is fully behind (away from target) the vertical line from the ball
Too far forward: any part of the golfer's head is not behind (away from target) the vertical line
Too far back: target side of the golfer's head is more than 6 inches behind (away from target) the vertical line
Click the "Accept" button after making choice to accept and move to the next option.
Shaft Option:
Choices: "OK" or "Too vertical"
OK: shaft of the club should be on the line or no farther away than instructor's
Too vertical: shaft of club is farther above the line than instructor's
Click the "Accept" button after making choice to accept and move to the next option.

In the preferred embodiment, the entire process of key framing and editing takes only a few minutes. However, through additional prompts, menu choices, and automation, one skilled in the art could reduce this time even further.

Figure 11:
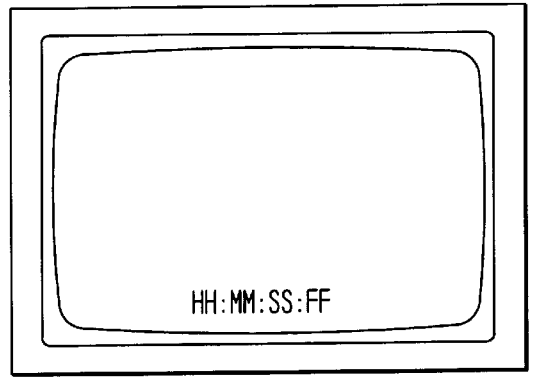
FIG. 11 is a shot of the input master selection screen on the monitor in the trailer unit shown in FIG. 9.
Figure 12:
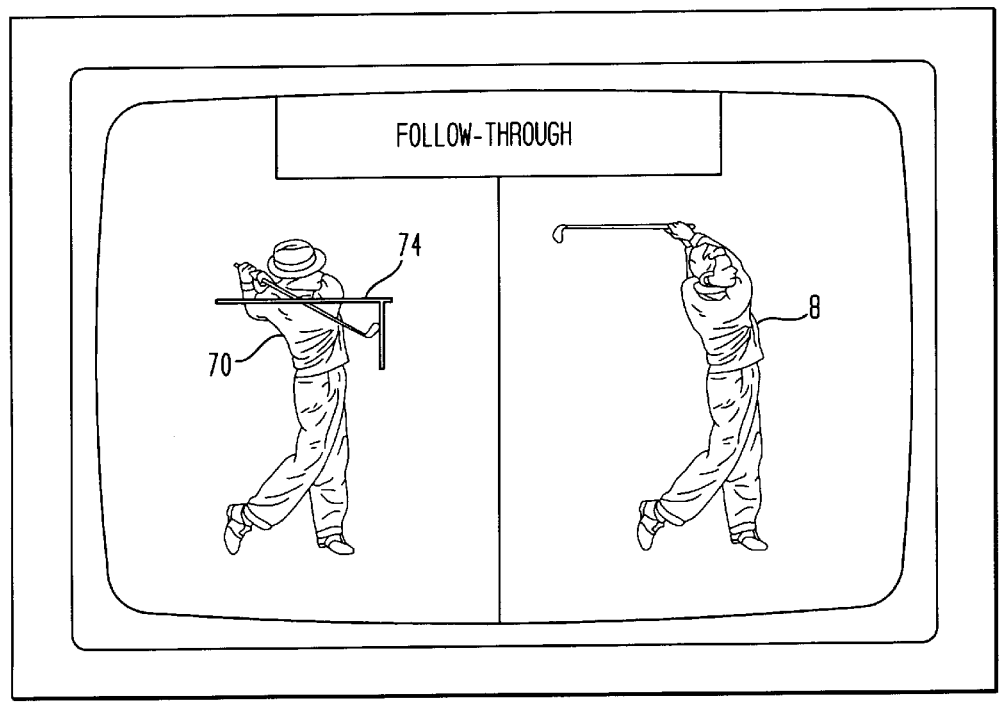
FIG. 12 is a shot of the key frame screen on the monitor shown in FIG. 9.

After this process, the operator clicks on the edit button and returns to the main input screen, FIG. 11. The operator moves the student golfer's name from the edited list by clicking on the name and dropping it into the first available VCR slot by clicking on a VCR slot in the grid in the lower right corner of FIG. 11. At the same time, printer 659 (FIG. 10) produces a label imprinted with the golfer's name. When dropped into the grid the input computer 615 transfers from computer 615 to the selected one of computer 617–629. The selected student golfer's files from the high media disk 645 into directory "control/AVIS/" as files "g.list," "gb.avi" and "gf.avi" on the selected one of output computer 617–629.

The operator selects the appropriate partially recorded videotape. In accordance with the present invention the operator has a choice of a plurality of different tapes. The student golfer and the operator at the tee previously selected the desired video, e.g., male, female, senior, left-handed, right-handed, etc. The operator inserts the partially recorded videotape into the VCR that the operator had just selected for that student golfer and places the printed label with the golfer's name in a slot on the outside of that VCR.

The operator then uses selector boxes 649 and 650 to output that VCR for the tape that the operator just started onto monitors 653 and 655. While key framing and editing the next student golfer, the operator monitors the tape then started on monitor 655 to insure that the tape is running, the logo and the split screen is centered, the video insertions are dropped into the appropriate gaps, and the picture and sound quality is satisfactory.

The selected output computer commences post processing to eliminate the double image (motion artifact) in the full swing video. The selected one of output computers 617–629 removes one field in each frame of the student golfer's video. It then duplicates each line in the remaining field to construct a non-interlaced frame. The post processing process creates these two new files xga.avi and xgb.avi. Although the preferred embodiment eliminates the field in each frame prior to activating VCR's 631–643, one skilled in the art will recognize that this step is also susceptible to the dynamic processing techniques of the present invention, and thus could be accomplished as the partially pre-recorded videotape is advanced from one gap to the next.

Output computers 617–629 are then ready to transfer the student golfer's video onto the partially pre-recorded videotape. Two types of VCR's have been used in the preferred embodiment. The JVC BR-S8000 and the Sanyo GUR-S955. The selected output computer 617–629 controls its associated VCR through its RS232 interface. Of course, any suitable VCR that can operate under computer control and has the ability to recognize these codes should be satisfactory.

Two time codes are presently used: VITC (vertical interval time code) and LTC (linear time code). The VITC time code is impressed upon the video signal in a non-visible range. LTC is an audio signal, and unless overwritten, will generally be audible on the finished tape. Through a file, "output control.txt" in the preferred embodiment, output computers 617–629 know which type of time code its associated VCR uses.

The operation of the VCR is now described. For purposes of illustration the output computer 617 and VCR 631 are discussed; other pairs operate similarly. Output computer 617 starts the VCR 631 and fast forwards it to five seconds before the start of the first gap. Output computer 617 then stops and slow forwards VCR 631 until the beginning of the first gap. At that point it inserts onto the partially prerecorded videotape the first video segment for the student golfer.

After placing the first segment of the student golfer on the videotape, the computer advances the VCR to the position in which the next segment will be inserted. It continues doing this until all the gaps on the videotape are filled. When computer 617 has finished inserting the golfer's frames into the appropriate gaps in the videotape, it instructs VCR 631 to eject the completed videotape.

As is evident from the description below the preferred embodiment creates the segments for insertion into the gaps dynamically, preferably during the period that the videotape is moving from one gap to the next. Accordingly, no production time is lost awaiting the creation of the video and audio segments; the insertions are produced "real time" during the movement of the partially pre-recorded videotape through the VCR. There is no need to stop the recording process to await the creation of the segments for insertion. The present invention thus permits the production of more completed instructional videotapes in a shorter period.

FIG. 15 summarizes the process flow in trailer unit 601. At step 801 the operator loads the high capacity removable media into drive 645 of computer 615. Input computer move the appropriate golfer's files off the high capacity removable media in drive 645 into its memory. The operator appropriately edits each frame and indicates the points for telestrations to the computer through use of the mouse 657 and the video monitor 653. At step 809 the edited files are transferred to the selected one of output computer 617–629. In step 811 the operator selects and inserts the proper partially prerecorded video tape in the selected output computer, and in step 813 the selected output computer inserts the video frames in accordance with the present invention into the gaps of partially prerecorded videotape 1. Finally at step 815 the selected VCR ejects tape 1.

In providing telestrations on the video, the computer dynamically creates the telestrations during processing. The instructor's and student golfer's frames upon which the telestration is to be superimposed are placed into buffers. The telestration is then drawn upon the image in the buffer and the combined telestration and image are blasted both to monitor 653 and the VCR associated with the particular computer. This process is repeated as necessary for each frame.

The preferred embodiment of the present invention dynamically creates the video and audio frames that are recorded onto the partially prerecorded videotape using the ASCII configuration file that was created at the tee unit 500 and in the trailer unit 601 during the key framing and editing process on input computer 615. As described above the configuration file for each golfer contains the data for that golfer, e.g., selected lesson, type of stance, key frames, the telestration coordinates. From the configuration file each output computer 617–629 generates a script of computer commands for the particular student golfer that it is then processing. The output computer then reads the commands in that script to generate the video frames that are inserted into the gaps on the partially pre-recorded videotape.

By way of example this explanation describes the operation in conjunction with output computer 617 and VCR 631, but a person of skill in the art will readily extend this example to the other ones of output computers 619–629 and VCR's 639–643. FIG. 16 illustrates the steps in generating the video frames to be inserted in the videotape. In the preferred embodiment, computer 617 is under control of a program written in Visual Basic, C and C++, although any other general-purpose computer language would be suitable. In step 701 of FIG. 16 the above described configuration file is read. The program in step 703 then running on output computer 617 assigns variables to many of the parameters in the configuration file.

At step 705 output computer 617 determines from the appropriate variable created from the configuration file which golf lesson computer 617 is to build. Computer 617 then branches to run the instructions associated with that lesson, and at step 707 starts to build the script file for the first gap on the partially pre-recorded videotape. The present invention next creates for many of the gaps the variables that are specific to that gap as illustrated at step 707 of FIG. 13. Thus for example, in the case where the student golfer is a "leverage" golfer, computer 617 may assign to a variable representing the sound track for that gap a particular ".wav" file that contains the instructor's advice for a leverage golfer. On the other hand if the student golfer is an "arc" golfer, computer 617 would assign to that variable a different ".wav" file.

The preferred embodiment then at step 707 creates a script file by substituting for the template variables in pre-written computer commands the values of the variables that were created at steps 703 and 707. In FIG. 17 is shown code 751 that would form such code with template variables according to the present invention. Each line of code consists of a number of commands with template variables for which will be substituted the information from configuration file. For example, line 25 of code in FIG. 17 contains the instruction "print, Str$(gpos) & golfname".

That line includes the instruction "print". At step 709 of FIG. 16 that command will cause computer 617 to print the golfer's name starting at the position "gpos".

After executing the script, computer 617 then determines at step 711 whether the lesson is complete, i.e., all gaps have been filled. If not, computer 617 continues at step 707 to build the script for the next gap. Otherwise, computer 617 ejects the completed videotape at step 713 and stop executing at 715.

For example, in the preferred embodiment the particular golfer for which computer 617 is to construct a script may be a "leverage" "male" "left handed" golfer named "Fred" who wants to purchase the "basic golf lesson". The parameters "leverage", "male", "left handed", "Fred", and "basic" are stored in the configuration file. Under these circumstances, in step 703 the computer assigns to a variable "LessonType" the value "basic". It may also assign in this step the parameters "leverage", "male", "Fred" and "left handed" to the variables "gbody", "sex", "golfname" and false to "curgolferright". For step 707 the computer set other more gap specific variables dependent on the variable that have already been set. For example, the following codes sets a graphic and audio passage dependent on information that had been stored in the configuration file.

```
If gbody = "Leverage" Then
        v1 = "c:\sound\b231.wav"
        graphic = "c:\graphics\lleverage.tga"
    ElseIf gbody = "Arc" Then
        graphic = "c:\graphics\larc.tga"
            If curgolferright = True Then
                v1 = "c:\sound\b23a.wav"
            Else
                v1 = "c:\sound\left23a.wav"
            End If
    Else
        graphic = "c:\graphics\lwidth.tga"
        v1 = "c:\sound\b23w.wav"
    End If
```

Computer 617 then dynamically writes the script file that will create the inserts for the gaps on videotape 1. For each gap computer 617 has one or more template files in the form of template code 751 in FIG. 17. As one skilled in the art recognizes each line in template code 751 starts with the instruction "myguide.Additem" which causes the following textual material to be written to a list (not shown), which computer 617 subsequently executes. The first line, "pos, golfer,403,0,320,440" has no variables; when executed this line tell computer 617 to position the image of the golfer in a rectangle having a corner at coordinates (403, 0) and horizontal and vertical extants of 320 and 440, respectively.

Line 3 contains the variable "v1". As describe above that variable had been set to the file "c:soundleft23a.wav" in step 707. Starting at line 6 of template code 751, based upon the variables of the present example (male golfer, leverage, left handed), the computer will produce the instructions "load, 730,model, c:norlbp231wtga" and "refresh1,730". The last line shown in template codes 751 creates an instruction to draw a telestration line based upon variables that were set in step 703.

The invention has been described and illustrated in connection with preferred embodiments. To those skilled in this art many variations and modifications will be evident and may be made without departing from the spirit and scope of the invention. The invention as set forth in the appended claims is thus not to be limited to the precise details of methodology or construction set forth above as such variations and modification are intended to be included within the scope of the appended claims.

What is claimed is:

1. A method for producing a personalized sports activity instructional videotape on a computer from a prerecorded instructional videotape about the sport activity having at least one gap and a plurality of instructional video segments which each address an aspect of the sports activity as performed by different persons, the method comprising:

recording in a first computer file a plurality of video frames of a person's performance of a sports activity;

recording in a second computer file information about said person;

selecting frames from said video frames from the first computer file which most closely match predetermined postures of the sports activity;

recording in said second computer file coordinates in at least some of said selected frames of predetermined points of said person or implements used in said sports activity;

selecting segments from said instructional video segments based upon the information in said second computer file;

combining said selected instructional video segments with at least one of said selected frames into a series of video frames;

inserting said series of video frames into said gap in said videotape.

2. A method for producing a personalized sports activity instructional videotape according to claim 1 wherein said step of recording in a first computer file a plurality of video frames includes the steps of:

storing in memory of a first computer each of said video frames; and storing in the same location in the memory of said first computer in which an oldest of said video frames is stored after more than a predetermined number of said video frames have been stored.

3. A method for producing a personalized sports activity instructional videotape according to claim 1 wherein said video frames comprise at least two interlaced fields and including the steps of:

deleting one field from at least one of the plurality of video frames;

duplicating each scan line in the at least one remaining field in said video frames; and inserting said duplicated scan line adjacent to the respective scan line duplicated.

4. A method for producing a personalized sports activity instructional videotape according to claim 1 wherein inserting said series of video frames includes the steps of:

advancing the videotape at a first rate until a point before the gap is reached;

advancing the videotape at a second rate, slower than said first rate, until the edge of the gap is reached; and recording into the gap said series of video frames.

5. A method for producing a personalized sports activity instructional videotape according to claim 4 wherein advancing the videotape comprises searching for predetermined time codes prerecorded on the partially prerecorded videotape.

6. A videotape made according to the method of claim 5 wherein the predetermined time codes are prerecorded in the video signal.

7. A method for producing a personalized sports activity instructional videotape according to claim 1 wherein the step of selecting said video frames comprises selecting one still frame which most closely matches each of said predetermined postures of the sports activity.

8. A method for producing a personalized sports activity instructional videotape according to claim 1 further including a plurality of video frames recording an instructor's performance of the activity and further comprising the step of:

including in at least one of said gaps a full motion visual recording simultaneously displaying both the person's performance of the activity and a full motion recording of instructor's performance of the activity.

9. A method for producing a personalized sports activity instructional videotape according to claim 8 further comprising the step of:

selecting frames from said first computer file showing said person's posture in the activity that substantially correspond to the position of the instructor in a frame from said video frames recording the instructor's performance of the activity to substantially match the pace of the full motion recording of the person's performance of the activity to the instructor's performance of the activity.

10. A method for producing a personalized sports activity instructional videotape according to claim 9 wherein the step of adjusting the pace of the full motion visual recording of the person's performance includes the steps of:

selecting video frames of the person's performance for each of said predetermined postures of the sports activity;

determining the number of frames between each of said predetermined postures in the instructor's performance of the activity;

inserting between consecutive frames of said predetermined postures in the person's performance of the sport's activity the same number of frames that are between said predetermined postures in said instructor's performance of the activity.

11. A method for producing a personalized golf instructional videotape on a computer from a prerecorded instructional golf videotape having at least one gap and a plurality of instructional video segments which each address an aspect of a golf swing as performed by different golfers each having different characteristics, the method comprising:

recording video frames into a first computer file in a first computer of a person's swing;

recording in a second computer file in said first computer information about in said person, at least some of which relates to the characteristics of the person's swing;

moving said first and second computer files from said first computer to a second computer;

selecting in said second computer from said first computer file those frames which most closely match predetermined postures of the golf swing;

recording in said second computer file in said second computer additional information, at least some of which relates to the characteristics of the person's swing;

selecting segments from said instructional video segments based upon information in said second computer file;

combining said selected instructional video segments with at least one of said selected frames into a series of video frames; and inserting said series of video frames into said gap in said videotape.

12. A method for producing a personalized golf instructional videotape according to claim 11 wherein the step of moving said first and second computer files from said first computer to said second computer includes:

transferring said files from the memory of said first computer to a removable storage media;

transporting said removable storage media to said second computer; and transferring said files from said removable storage media to the memory of said second computer.

13. A method for producing a personalized golf instructional videotape on a computer from a prerecorded instructional golf videotape having at least one gap and a plurality of instructional video segments which each address an aspect of a golf swing as performed by different persons, the method comprising:

recording video frames in a first computer file of a person's swing;

recording in a second computer file information about said person, at least some of which relates to the characteristics of the person's swing;

selecting from said first computer file those frames which most closely match predetermined postures of the golf swing;

selecting segments from said instructional video segments based upon information in said second computer file;

combining said selected instructional video segments with at least one of said selected frames into a series of video frames;

inserting said series of video frames into said gap in said videotape.

14. A method for producing a personalized golf instructional videotape according to claim 13 wherein said selecting segments from said instructional video segments includes the steps of:

examining each field of each of said frames;

selecting the frame which most closely matches said predetermined postures of the golf swing.

15. A method for producing a personalized golf instructional videotape according to claim 13 wherein each of said video frames consists of two interlaced fields including the steps of:

removing one field from each frame;

duplicating each line in the remaining field; and inserting the duplicated line adjacent to the line duplicated, respectively.

16. A method for producing personalized golf instructional videotape according to claim 15 wherein the step of inserting each duplicated line comprises inserting said duplicated line immediately below the line that it duplicates.

17. A method for producing personalized golf instructional videotape according to claim 13 wherein a first computer is in close proximity to a golf tee and a second computer is a location remote from said golf tee.

18. A method for producing personalized sports activity instructional videotape under computer control from a partially prerecorded instructional videotape about the sport activity that employs at least one piece of equipment, said partially prerecorded videotape having at least one gap, and a plurality of instructional video segments which each address an aspect of the sports activity as performed by different persons, each with different characteristics, the method comprising:

recording in a first computer file a plurality of frames of a person's performance of a sports activity;

recording in a second computer file information about said person;

selecting from first computer file those frames which most closely match predetermined postures assumed by a person during the performance of the sports activity;

recording in said second computer file coordinates in at least some of said selected frames of predetermined postures of said person or said equipment used in said sports activity;

generating a sequence of computer instructions from said information in said second computer file to select at least one of said segments from said instructional video segments and at least one of said selected frames to construct a series of video frames to insert into said gap in said prerecorded instructional videotape;

inserting said series of video frames into said gap in said videotape.

19. A method for producing a personalized sports activity instructional videotape according to claim 18 wherein said step of generating a sequence of computer instructions includes:

reading a first set of computer instructions into memory, at least some of which instructions have variables;

reading said second computer file; and substituting for said variables information from said second computer file.

20. A method for producing a personalized sports activity instructional videotape according to claim 18 including a plurality of audio segments which each address an aspect of the sports activity as performed by different persons and including the steps of:

generating a sequence of computer instructions from said information in said second computer file to select at least one of said audio segments to insert into said gap in said partially prerecorded instructional videotape.

21. A method for producing a personalized sports activity instructional videotape according to claim 19 wherein said partially recorded video tape has a plurality of gaps and wherein said step of generating a sequence of computer instructions dynamically occurs before inserting said series of video frames into a gap in said videotape and after video frames have been inserted into all prior gaps on said videotape.

22. A system for producing a personal golf lesson video comprising:

two or more cameras for recording a person's golf swing;

first capture and memory means connected to each of the two or more cameras for capturing and storing the recorded golf swing into first files on each of the capture and memory means;

second capture and memory means to enter and store information in a second file about the person's swing whose swing is recorded;

first selection means for selecting from first computer files video frames which most closely match predetermined postures of the golf swing;

second selection means for selecting segments from said instructional video segments based upon information in said second computer file;

partially prerecorded videotape golf lesson having gaps in predetermined locations;

video recording device for copying the selected segments into the gaps of the prerecorded videotape golf lesson.

23. The system of claim 22 wherein at least one of the first and second capture and memory means comprise a computer readable memory for storing digitized golf swing images.

24. A method for producing a personalized sports activity instructional videotape on a computer from a prerecorded instructional videotape about the sport activity having at least one gap and a plurality of video frames recording an instructor's performance of the activity, the method comprising:

recording in a first computer file a plurality of video frames of a person's performance of a sports activity;

selecting frames from said first computer file showing said person's posture in the activity that substantially correspond to the position of the instructor in a frame from said video frames recording the instructor's performance of the activity to substantially match the pace of the full motion recording of the person's performance of the activity to the instructor's performance of the activity;

combining each of said selected frames of said person's performance and the corresponding frame of the instructor's performance into single frame showing both the person and the instructor in substantially the same posture;

combining selected instructional video segments with at least one of said selected frames into a series of video frames;

inserting said series of combined video frames into said gap in said videotape to produce a person's performance of the activity that substantially matches the instructor's performance of the activity.

* * * * *